United States Patent [19]
Dutot

[11] Patent Number: 5,840,757
[45] Date of Patent: Nov. 24, 1998

[54] LIPID EMULSION INTENDED FOR PARENTERAL OR ENTERAL FEEDING

[75] Inventor: Guy Dutot, Noisy le Roi, France

[73] Assignee: Clintec Nutrition Company, Deerfield, Ill.

[21] Appl. No.: 755,610

[22] Filed: Sep. 5, 1991

Related U.S. Application Data

[63] Continuation of Ser. No. 453,359, Dec. 19, 1989, abandoned, which is a continuation of Ser. No. 223,120, Jul. 22, 1988, abandoned.

[30] Foreign Application Priority Data

Jul. 23, 1987 [FR] France .................................. 87 10407

[51] Int. Cl.⁶ .................................................. A61K 31/20
[52] U.S. Cl. .......................................... 514/560; 514/932
[58] Field of Search ..................... 514/560, 784, 514/785, 937

[56] References Cited

U.S. PATENT DOCUMENTS

| | | | |
|---|---|---|---|
| 2,819,199 | 1/1958 | Kalish . | |
| 3,085,939 | 4/1963 | Wruble et al. ........................... | 514/938 |
| 4,481,185 | 11/1984 | Grollier et al. ......................... | 514/938 |
| 4,703,062 | 10/1987 | Blackburn et al. ..................... | 514/938 |

FOREIGN PATENT DOCUMENTS

| | | |
|---|---|---|
| 0189160 | 7/1986 | European Pat. Off. . |
| 0216419 | 4/1987 | European Pat. Off. . |
| 2 067 587 | 7/1981 | United Kingdom . |
| 8402271 | 6/1984 | WIPO .................................... 514/938 |
| WO 86/1715 | 3/1986 | WIPO . |

OTHER PUBLICATIONS

FAO Food and Nutrition Paper 3, Dietary Fats and Oils in Human Nutrition, Report of an Expert Consultation Held in Rome 21–30, Sep. 1977, pp. 19–36.

A. Shenkin et al., Wld. Rev. Nutr. Diet., vol. 28, 1978, pp. 34–35, 40, 44–45, and 49.

R.E. McClead, Jr. et al, Journal of Pediatric Gastroenterology and Nutrition, vol. 4, pp. 234–239, 1985.

Z. Fredmann et al, Pediatrics, vol. 61, No. 5, May 1978, pp. 694–698.

Friedman, *Essential Fatty Acids Revisited*, Am J Dis Child, vol. 134, pp. 397–408 (1980).

Wan et al, *Effect of dietary linoleate content on the metabolic response of rats to escherichia coli endotoxin*, Clinical Science, vol. 72, pp. 383–385 (1987).

Mattson et al, *Comparison of effects of dietary saturated, monounsaturated, and polyunsaturated fatty acids on plasma lipids and lipoproteins in man*, Journal of Lipid Research, vol. 26, pp. 194–202 (1985).

Grundy, *Monounsaturated fatty acids, plasma cholesterol, and coronary heart disease*, Am J Clin Nutr, vol. 45, pp. 1168–1175 (1987).

Primary Examiner—Leonard Schenkman
Attorney, Agent, or Firm—Hill & Simpson

[57] ABSTRACT

A lipid emulsion suitable for use as a parenteral or enteral foodstuff, wherein the lipid phase is a mixture of long-chain fatty acids in which 15 to 45% of the total fatty acids are essential fatty acids.

16 Claims, No Drawings

LIPID EMULSION INTENDED FOR PARENTERAL OR ENTERAL FEEDING

This application is a continuation of application Ser. No. 453,359, filed Dec. 19, 1989, now abandoned, which is a continuation of application Ser. No. 223,120, filed Jul. 22, 1988, now abandoned.

The present invention relates to a lipid emulsion suitable for use as a parenteral or enteral foodstuff and to compositions containing it.

Justification for the use of lipids in parenteral feeding rests on the following arguments:

a mixed carbohydrate/Lipid intake is more physiological than an exclusive carbohydrate intake, lipids supply essential fatty acids which the body is incapable of synthesizing, a high calorific power combined with a low osmolarity enables a large amount of calories to be administered peripherally in a small volume.

The soybean and safflower oils currently used in injectable lipid emulsions are characterized by a high content of polyunsaturated fatty acids (approximately 60 % and 75 %, respectively), which enable the essential fatty acid requirements of patients needing intravenous feeding to be covered amply.

However, in the context of total parenteral feeding, where the lipid intake represents 30 to 50% of the carbohydrate/lipid calories, the composition of these oils is unsuitable for the following reasons:

the high proportion of essential fatty acids appears likely to inhibit partially their desaturation/elongation to form active higher metabolites (S. INNIS, Lipids, 1986, 21, 132–138).

the high linoleic acid content of these oils has been held responsible for immuno-suppressant effects, which may interact with the inflammatory phenomena pre-existing in patients in a stress situation.

the fatty acid composition of safflower and soybean oils makes them very sensitive to peroxidation.

LinoLeic and α-linolenic acids are very sensitive to peroxidation as a result of the presence of several double bonds in their structure. The peroxidation of fatty acids generates the formation of various compounds which are poorly metabolized by the body.

Some oxidation derivatives of fatty acids react with proteins to give rise to fluorescent condensation products known as lipofuscins, which deposit in the tissue. Such treatments have been described in the context of parenteral feeding.

According to some authors, they could be responsible for certain liver abnormalities observed in patients receiving parenteral feeding.

An increase in lipid peroxidation during the administration of lipid emulsions has been demonstrated both in man and in animals (J. R. WISPE, Ped., 1985, 19, 374–379). These peroxidation phenomena risk being magnified in subjects in a stress situation, where the production of free radicals is increased with, in some instances, a decrease in activity of the antioxidant protection mechanisms (M. HIRAMATSU, Burns, 1984, 11, 111–116).

The present invention seeks to provide a more balanced Lipid emulsion having a lower content of poly-unsaturated fatty acids, which, while ensuring that the essential fatty acid requirements are covered, has the following advantages:

better utilization of the essential fatty acids to form their higher derivatives, avoiding the risk of inhibition of conversion of the fatty acids by excess substrate, smaller intake of polyunsaturated fatty acids, enabling lipid peroxidation to be limited, in particular in subjects suffering from inflammatory syndromes, with the production of free radicals.

The present invention provides a lipid emulsion suitable for use as a parenteral or enteral foodstuff, wherein the lipid phase is a mixture of long-chain fatty acids in which 15 to 45% of the total fatty acids are essential fatty acids.

The lipid phase preferably comprises a mixture of two or more oils selected from apricot, almond, groundnut, avocado, wheat, safflower, rapeseed, coconut, cottonseed, lupin, maize, hazelnut, walnut, olive, oenothera, palm, palm-kernel, peach, grape, rice, rye, sesame, soybean, sunflower, tomato, linseed and citrus oils.

Examples of suitable lipid phases are shown below in a Table.

TABLE

| LIPID PHASE (MIXTURE OF OILS) | Essential fatty acids as % of total fatty acids |
|---|---|
| AVOCADO (46%) - SOYBEAN (54%) | 40 |
| OLIVE (47%) - SOYBEAN (53%) | 40 |
| AVOCADO (60%) - WALNUT (40%) | 40 |
| AVOCADO (89%) - WALNUT (11) | 20 |
| WALNUT (11%) - OLIVE (89%) | 26 |
| OLIVE (85%) - SOYBEAN (15%) | 20 |
| WALNUT (40%) - OLIVE (60%) | 40 |

Variations in the composition of the oils may be observed in accordance with their origin. The mixtures will hence be adapted to obtain the requisite essential fatty acid composition.

The lipid emulsions of the invention are preferably emulsions in water, for example comprising from 5 to 50% by weight, relative to the total weight of the emulsion, of the lipid phase in water. The emulsions may contain emulsifying agents, for example, plant, animal or synthetic phospholipids, which are generally present in a proportion of from 0.5 to 5% by weight, relative to the total weight of the emulsion.

The lipid emulsion of the invention may also, for example, comprise a tonicity-regulating agent such as glycerol, glucose, a polyol or an amino acid.

The lipid emulsion of the invention may be used as an enteral or parenteral foodstuff as it is, or as a lipid constituent of a complete emulsion or solution, which may also, for example, comprise amino acids, carbohydrates, vitamins, carnitine, trace elements or keto analogues of amino acids.

The present invention also provides a pharmaceutical composition which comprises a lipid emulsion as defined above and a solvent or adjuvant. The present invention further provides a dietetic composition which comprises lipid emulsion as defined above and a solvent or adjuvant.

The lipid emulsions of the invention may be used for achieving a parenteral or enteral intake of calories and of essential fatty acids when oral feeding is impossible.

I claim:

1. A lipid emulsion suitable for use as a parenteral or enteral foodstuff, comprising from 5 to 50% by weight, relative to the total weight of the emulsion, of a lipid phase in water, said lipid phase consisting essentially of a mixture of long-chain fatty acids in which 15 to 45% by weight of the total fatty acids are essential fatty acids, the essential fatty acids being linoleic acid and α-linolenic acid.

2. A lipid emulsion according to claim 1 wherein the lipid phase comprises a mixture of two or more oils selected from the group consisting of apricot, almond, groundnut, avocado, wheat, safflower, rapeseed, coconut, cottonseed, lupin, maize, hazelnut, walnut, olive, oenothera, palm, palm-kernel, peach, grape, rice, rye, sesame, soybean, sunflower, tomato, linseed and citrus oils.

3. A lipid emulsion according to claim 2 wherein the lipid phase comprises, by weight, about 46% avocado oil and about 54% soybean oil.

4. A lipid emulsion according to claim 2 wherein the lipid phase comprises, by weight, about 47% olive oil and about 53% soybean oil.

5. A lipid emulsion according to claim 2 wherein the lipid phase comprises, by weight, about 60% avocado oil and about 40% walnut oil.

6. A lipid emulsion according to claim 2 wherein the lipid phase comprises, by weight, about 89% avocado oil and about 11% walnut oil.

7. A lipid emulsion according to claim 2 wherein the lipid phase comprises, by weight, about 11% walnut oil and about 89% olive oil.

8. A lipid emulsion according to claim 2 wherein the lipid phase comprises, by weight, about 85% olive oil and about 15% soybean oil.

9. A lipid emulsion according to claim 2 wherein the lipid phase comprises, by weight, about 40% walnut oil and about 60% olive oil.

10. A lipid emulsion according to claim 1 which further comprises, as an emulsifying agent, from 0.5 to 5% by weight, relative to the total weight of the emulsion, of plant, animal or synthetic phospholipids.

11. A lipid emulsion according to claim 1 which further comprises a tonicity-regulating agent.

12. A lipid emulsion according to claim 11 wherein the tonicity-regulating agent is selected from the group consisting of glycerol, glucose, a polyol and an amino acid.

13. An emulsion or solution comprising a lipid emulsion as defined in claim 1 and a solvent or adjuvant.

14. An emulsion or solution according to claim 13 wherein the emulsion or solution contains a pharmaceutically active ingredient.

15. An emulsion or solution according to claim 13 wherein the emulsion or solution is a dietetic composition.

16. A lipid emulsion suitable for use as a parenteral or enteral foodstuff, comprising from 5 to 50% by weight, relative to the total weight of the emulsion, of a lipid phase that comprises a mixture of at least two oils in water, said lipid phase consisting essentially of a mixture of long-chain fatty acids in which 15 to 45% by weight of the total fatty acids are essential fatty acids, the essential fatty acids being linoleic acid and α-linolenic acid.

* * * * *